US008602556B2

(12) United States Patent
Imamura

(10) Patent No.: US 8,602,556 B2
(45) Date of Patent: Dec. 10, 2013

(54) IMAGE PROCESSING APPARATUS AND IMAGE PROCESSING SYSTEM FOR DISPLAYING INFORMATION ABOUT OCULAR BLOOD FLOW

(75) Inventor: Hiroshi Imamura, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/402,670

(22) Filed: Feb. 22, 2012

(65) Prior Publication Data

US 2012/0218517 A1 Aug. 30, 2012

(30) Foreign Application Priority Data

Feb. 25, 2011 (JP) ................................ 2011-040274

(51) Int. Cl.
*A61B 3/14* (2006.01)
(52) U.S. Cl.
USPC .............................. 351/206; 396/18; 600/504
(58) Field of Classification Search
USPC ............. 351/200–246; 396/18; 382/128–134; 356/496–498; 600/504
See application file for complete search history.

(56) References Cited

U.S. PATENT DOCUMENTS

2002/0131017 A1* 9/2002 Kishida et al. ................ 351/206
2007/0252951 A1* 11/2007 Hammer et al. .............. 351/221
2011/0234975 A1 9/2011 Hirose

FOREIGN PATENT DOCUMENTS

WO WO2009/015295 A1 1/2009

OTHER PUBLICATIONS

Johnny Tam, Austin Roorda, "Enhanced Detection of Cell Paths in Spatiotemporal Plots for Noninvasive Microscopy of the Human Retina", Proceedings of 2010 IEEE International Symposium on Biomedical Imaging, pp. 584-587, Apr. 2010.
Johnny Tam, Austin Roorda, "Pulsatility of parafoveal capillary leukocytes", Experimental Eye Research 88 (2009) pp. 356-360.
Joy A. Martin, Austin Roorda, "Direct and Noninvasive Assessment of Parafoveal Capillary Leukocyte Velocity", 2005 by the American Academy of Ophthalmology, ISSN 0161-6420/05, vol. 112, No. 12, pp. 2219-2223.
Johnny Tam et al.,"Noninvasive Visualization and Analysis of Parafoveal Capillaries in Humans", Investigative Ophthalmology & Visual Science, Mar. 2010, vol. 51, No. 3, pp. 1691-1698.

* cited by examiner

*Primary Examiner* — Darryl J Collins
*Assistant Examiner* — Gary O'Neill
(74) *Attorney, Agent, or Firm* — Canon U.S.A., Inc., IP Division

(57) ABSTRACT

An image processing apparatus includes an identification unit configured to identify a retinal blood vessel based on a retinal image, a measurement unit configured to measure blood flow information for the blood vessel based on the retinal image, and a display control unit configured to display the measured blood flow information by at least one selected from a depth of the identified blood vessel, a size of the identified blood vessel, and a combination of both.

15 Claims, 13 Drawing Sheets

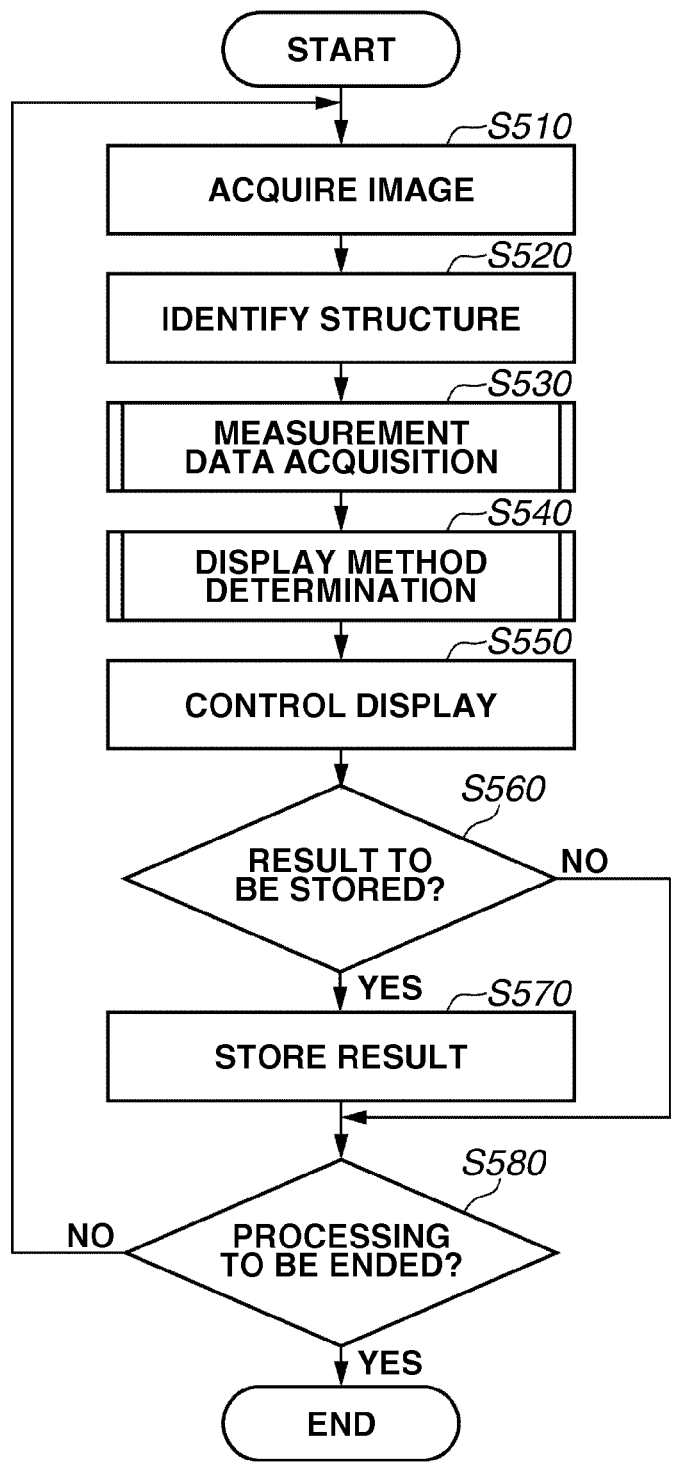

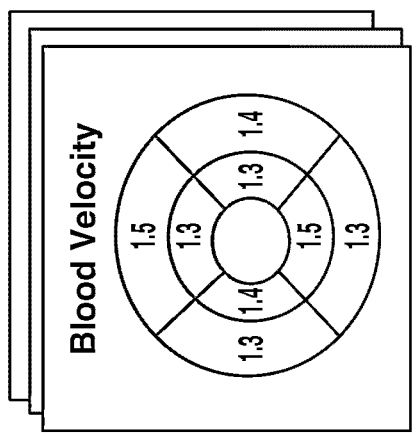
FIG.11A BY BLOOD VESSEL DIAMETER (BLOOD FLOW VELOCITY AT MACULAR AREA)
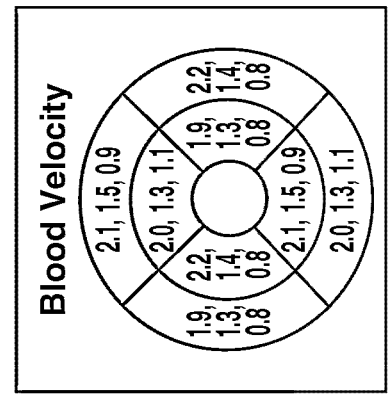
FIG.11B
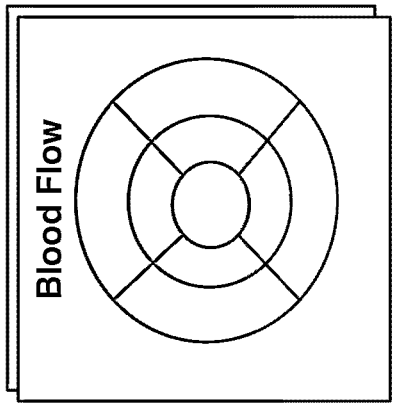
FIG.11C BY DEPTH POSITION (BLOOD FLOW RATE AT MACULAR AREA)

AGING GRAPH
(BLOOD FLOW RATE
AT OPTIC DISC)

BY DEPTH POSITION
(BLOOD FLOW RATE
AT OPTIC DISC)

COMPARISON
OF BOTH EYES
(BLOOD FLOW VELOCITY
AT OPTIC DISC)

IMAGE PROCESSING APPARATUS AND IMAGE PROCESSING SYSTEM FOR DISPLAYING INFORMATION ABOUT OCULAR BLOOD FLOW

TECHNICAL FIELD

The present disclosure relates to an image processing apparatus and an image processing system configured to display information about an ocular blood flow.

BACKGROUND

Ocular examinations are widely performed for the purpose of preemptive medical care for lifestyle-related diseases and other diseases occupying major causes of blindness. A scanning laser ophthalmoscope (SLO; hereinafter referred to as an SLO imaging apparatus), an ophthalmology apparatus based on the principle of a confocal laser scanning microscope, performs raster scan on a fundus with a laser beam (i.e., a measuring beam) and, based on the light intensity of a relevant return beam, quickly acquires a high-resolution retinal image.

In recent years, an adaptive optics (AO)-SLO imaging apparatus including an adaptive optics (AO) has been developed. The AO measures an aberration of the subject's eye in real time by a wavefront sensor and corrects the aberration of the measurement beam and its return beam occurring at the subject's eye by a wavefront compensation device. The thus-configured AO-SLO imaging apparatus can acquire a high lateral resolution image and accordingly detect retinal capillaries and visual cells.

As a method for comparatively displaying measurement results regarding blood vessels based on an ocular SLO image, a non-patent literature 1 (Johnny Tam, Joy A. Martin, and Austin Roorda, "Noninvasive visualization and analysis of parafoveal capillaries in humans", Investigative Ophthalmology and Visual Science, Vol. 51 No. 3, pp. 1691-1698, March 2010) discusses a technique for dividing a peripheral area of fovea centralis into four (top, bottom, left, and right) division areas centering on the fovea centralis with respect to a capillary extraction result and displaying the distribution density of capillaries in each division area (acquired by dividing the total length of blood vessels by the area for each division area).

Non-patent literature 2 (Johnny Tam and Austin Roorda, "Enhanced Detection of Cell Paths in Spatiotemporal Plots for Noninvasive Microscopy of the Human Retina", Proceedings of 2010 IEEE International Symposium on Biomedical Imaging, pp. 584-587, April 2010) discusses a technique for recognizing a blood cells' moving range as a blood vessel area based on an SLO image focused in the vicinity of visual cells of the healthy eye, and measuring the blood cells' moving velocity and other blood flow dynamic states.

However, blood vessels seem to exist at the same position when viewed from the anterior eye, they may exist at different positions in the depth direction (hereinafter referred to as depth positions). Therefore, the blood flow state cannot be correctly grasped simply by dividing the SLO image into partial areas and displaying them.

Another issue is that, since the blood vessel diameter varies from position to position, the blood flow state cannot be correctly recognized simply by dividing the SLO image into partial areas and displaying information about the blood flow.

SUMMARY

According to an aspect of the present embodiment, an image processing apparatus includes an identification unit configured to identify a retinal blood vessel based on a retinal image, a measurement unit configured to measure blood flow information for the blood vessel based on the retinal image, and a display control unit configured to display the measured blood flow information by at least one selected from a depth of the identified blood vessel, a size of the identified blood vessel, and a combination of both.

According to another aspect of the present embodiment, an image processing system includes an image processing apparatus including an identification unit configured to identify a retinal blood vessel based on a retinal image, a measurement unit configured to measure blood flow information for the blood vessel based on the retinal image, and a display control unit configured to display the measured blood flow information by at least one selected from a depth of the identified blood vessel, a size of the identified blood vessel, and a combination of both, and a display unit configured to display information according to control of the display control unit.

Further features and aspects of the present embodiment will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, and features together with the description, serve to explain the principles of the embodiment.

FIG. 5 is a flowchart illustrating processing performed by the image processing apparatus according to the exemplary embodiment.

FIGS. 11A to 11C illustrate the contents of measurement data displayed by a display control unit.

DESCRIPTION OF THE EMBODIMENTS

Various exemplary embodiments, and features will be described in detail below with reference to the drawings.

An image processing apparatus according to a first exemplary embodiment is configured to measure blood flow dynamic states based on an SLO moving image capturing capillaries around a fovea centralis, and to comparatively display statistical values for blood flow dynamic states for each local area in consideration of a blood vessel diameter, the number of pulsation cycles, and a depth position of the capillaries.

More specifically, the following two cases will be described below: (i) measure the blood flow velocity as a blood flow dynamic state, and comparatively display the measured blood flow velocity between local areas around the macular portion, and (ii) measure the blood flow rate as a blood flow dynamic state, and comparatively display the measured blood flow rate between layers at different depth positions.

[Entire Configuration]

Figure 1:
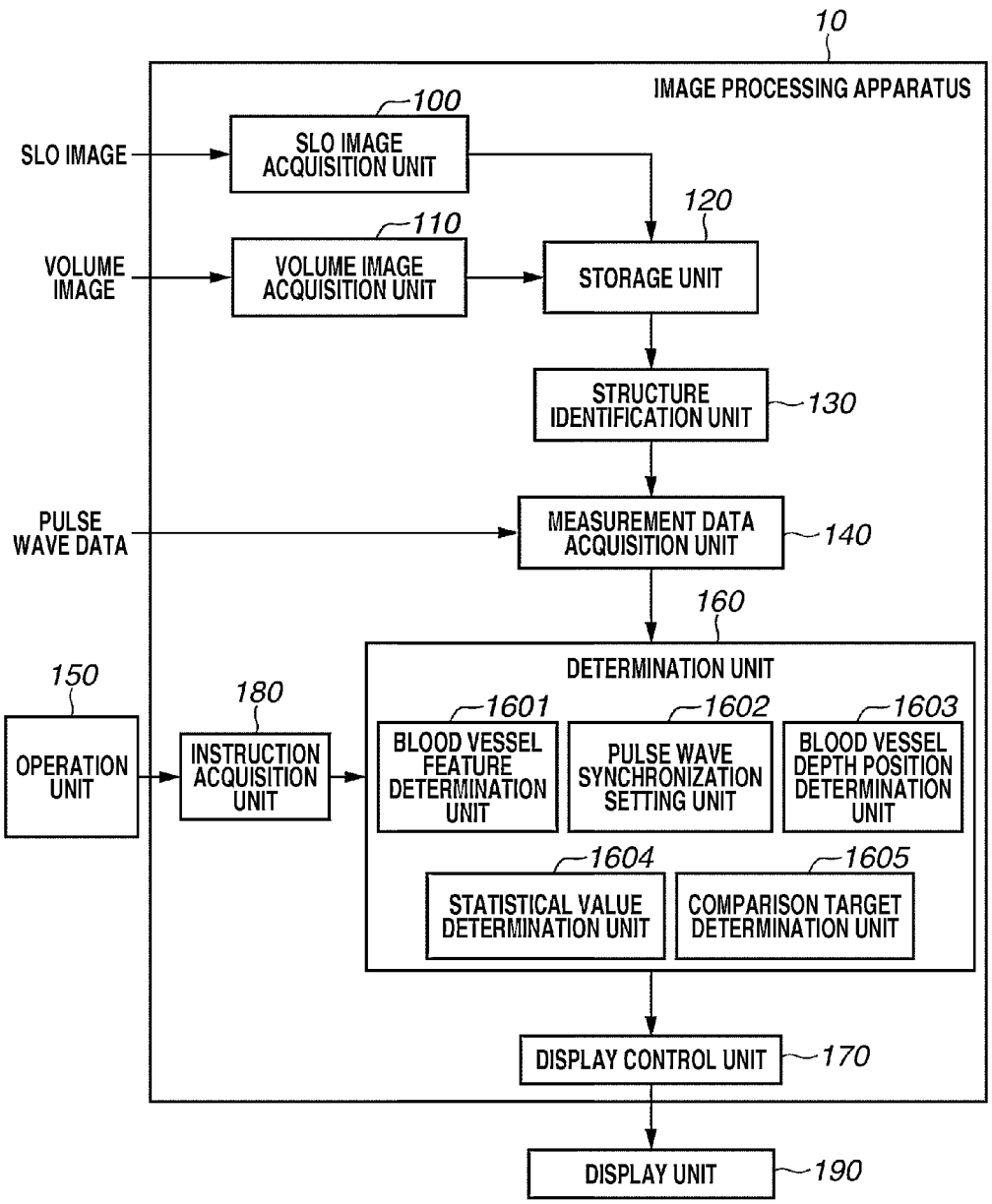
FIG. 1 is a block diagram illustrating an example functional configuration of an image processing apparatus according to an exemplary embodiment.

A functional configuration of an image processing apparatus 10 according to the present exemplary embodiment will be described below with reference to FIG. 1. FIG. 1 is a block diagram illustrating the functional configuration of the image processing apparatus 10. The image processing apparatus 10 includes an SLO image acquisition unit 100, a volume image acquisition unit 110, a storage unit 120, a structure identification unit 130, a measurement data acquisition unit 140, a determination unit 160, a display control unit 170, and an instruction acquisition unit 180. The image processing apparatus 10 further includes an operation unit 150 and a display unit 190 connected thereto.

The determination unit 160 includes a blood vessel feature determination unit 1601, a pulse wave synchronization setting unit 1602, a blood vessel depth position determination unit 1603, a statistical value determination unit 1604, and a comparison target determination unit 1605.

Figure 2:
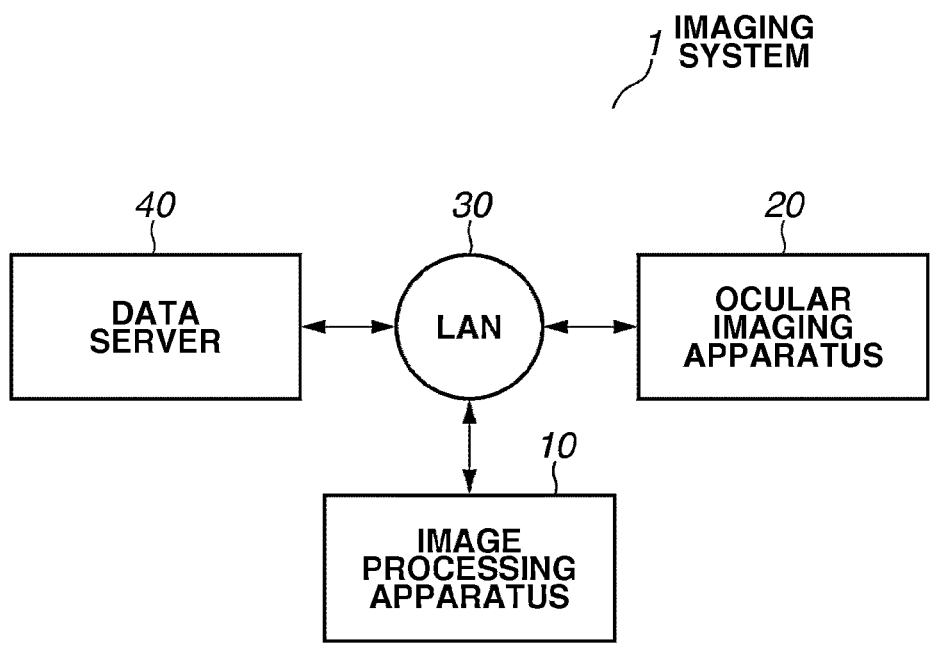
FIG. 2 is a block diagram illustrating an example configuration of an imaging system including the image processing apparatus according to the exemplary embodiment.

FIG. 2 is a block diagram illustrating an imaging system 1 including the image processing apparatus 10 according to the present exemplary embodiment. As illustrated in FIG. 2, the image processing apparatus 10 is connected with an ocular imaging apparatus 20 and a data server 40 via a local area network (LAN) 30. The LAN 30 may include optical fibers, universal serial buses (USBs), and Institute of Electrical and Electronics Engineers (IEEE) 1394 buses. The image processing apparatus 10 may be connected with these apparatuses via an external network such as the Internet.

The ocular imaging apparatus 20 includes an SLO imaging unit for capturing a planar image (SLO image) of a fundus, and an optical coherence tomography (OCT) imaging unit for capturing a volume image (OCT image) of the fundus. The ocular imaging apparatus 20 captures a still image or a moving image as an SLO image, and transmits the captured SLO image to the image processing apparatus 10 and the data server 40.

The OCT imaging unit can be configured, for example, on a time domain or Fourier domain basis to three-dimensionally capture a tomographic image of the subject's eye in response to an operation by an operator (not illustrated). The ocular imaging apparatus 20 transmits the acquired volume image to the image processing apparatus 10 and the data server 40. The ocular imaging apparatus 20 does not necessarily include the OCT imaging unit, and may include only the SLO imaging unit.

The image processing apparatus 10 acquires image features of the subject's eye (hereinafter referred to as ocular features) based on the SLO image and the OCT image acquired by the ocular imaging apparatus 20 and, based on the acquired ocular features, performs measurement processing for cells' dynamic states such as the blood flow velocity. The ocular imaging apparatus 20 transmits the acquired ocular features and the measurement data to the image processing apparatus 10 and the data server 40.

The data server 40 stores data related to the subject's eye, including the SLO image, the volume image, the ocular features (described below), pulse wave data, and fixation target position data at the time of SLO image capturing. The data server 40 stores the SLO image and volume image of the subject's eye output by the ocular imaging apparatus 20 and the ocular features output by the image processing apparatus 10. In response to a request from the image processing apparatus 10, the data server 40 transmits to the image processing apparatus 10 the data related to the subject's eye (SLO image, volume image, and ocular features), ocular feature normal value data, pulse wave data of the subject's eye, and fixation target position values at the time of image capturing.

In a case where the ocular imaging apparatus 20 includes only the SLO imaging unit and does not include the OCT imaging unit, the image processing apparatus 10 does not need to include the volume image acquisition unit 110. Although the image processing apparatus 10 according to the present exemplary embodiment includes the volume image acquisition unit 110 which is required to determine the depth position of capillaries, the image processing apparatus 10 does not include the volume image acquisition unit 110 if the depth position of capillaries is not to be distinguished.

Figure 3:
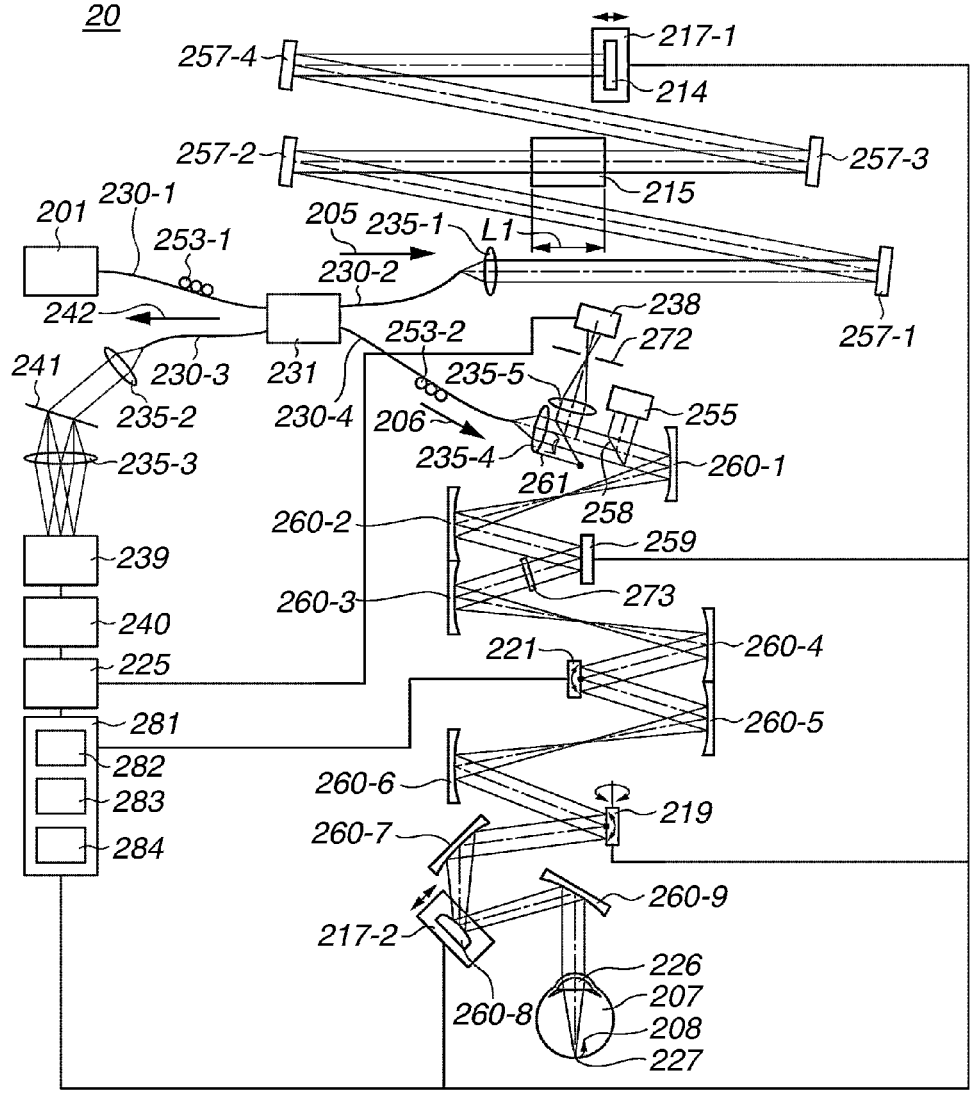
FIG. 3 illustrates an overall configuration of an ocular imaging apparatus according to the exemplary embodiment.

The ocular imaging apparatus 20 has an overall configuration illustrated in FIG. 3. The overview of the ocular imaging apparatus 20 will be described below.

[Overall Configuration]

Light emitted from a light source 201 is split into a reference beam 205 and a measurement beam 206 by an optical coupler 231. The measurement beam 206 is led to a subject's eye 207, as an object under observation, via a single mode fiber 230-4, a spatial light modulator 259, a XY scanner 219, an X scanner 221, spherical mirrors 260-1 to 260-9, and so on. The measurement beam 206 is reflected or scattered by the subject's eye 207 to become a return beam 208 and then enters a detector 238 or a line sensor 239. The detector 238 converts the light intensity of the return beam 208 into a voltage signal which is used to form a planar image of the subject's eye 207.

A combined wave of the reference beam 205 and the return beam 208 enters the line sensor 239 to form a tomographic image of the subject's eye 207. In this case, the wavefront aberration is preferably corrected, for example, by using a variable shape mirror.

[Light Source]

The light source 201 is a super luminescent diode (SLD), a typical low-coherence light source, having a wavelength of 830 nm and a bandwidth of 50 nm. In this case, a low-coherence light source is selected to acquire a planar image including few speckle noise. Although the SLD is selected as a light source, any type of light source element capable of emitting a low-coherence beam, such as an amplified spontaneous emission (ASE), can be used.

In consideration of ocular measurement, the wavelength of the near-infrared light is suitable. Further, since the wavelength affects the resolution in the horizontal direction (hereinafter referred to as lateral resolution) of the acquired planar image, the wavelength is desirably as short as possible. In this case, the wavelength is set to 830 nm. Other wavelengths may be selected according to a measurement region under observation. The SLD (low-coherence light source) is also suitable for capturing a tomographic image.

[Reference Optical Path]

An optical path of the reference beam 205 will be described below.

The reference beam 205 split by the optical coupler 231 is led to a lens 235-1 via a single mode fiber 230-2, and adjusted to become a parallel beam having a beam diameter of 4 mm.

Then, the reference beam 205 is led to a mirror 214, which serves as a reference mirror, by mirrors 257-1 to 257-4. An optical path length of the reference beam 205 is adjusted to be approximately the same as an optical path length of the measurement beam 206, and thus it is possible to cause interference between the reference beam 205 and the measurement beam 206.

Then, the reference beam 205 is reflected by the mirror 214 and then led again to the optical coupler 231. A dispersion compensation glass 215 through which the reference beam 205 passes, compensates the dispersion occurring when the measurement beam 206 has traveled to/from the subject's eye 207 with respect to the reference beam 205.

In this case, assuming an average diameter of the Japanese eyeball, L1 is set to 23 mm.

A motor-driven stage 217-1 can move in directions indicated by an arrow to enable adjusting and controlling the optical path length of the reference beam 205.

The motor-driven stage 217-1 is controlled by a personal computer 225 via a motor-driven stage drive driver 283 in a driver unit 281.

[Measurement Optical Path]

An optical path of the measurement beam 206 will be described below.

The measurement beam 206 split by the optical coupler 231 is led to a lens 235-4 via the single mode fiber 230-4, and adjusted to become a parallel beam having a beam diameter of 4 mm. A polarization controller 253-1 or 253-2 can adjust a polarization state of the measurement beam 206. In this case, the polarization state of the measurement beam 206 has been adjusted to linear polarization in the direction parallel to the paper surface.

The measurement beam 206 passes through a beam splitter 258 and a movable beam splitter 261, and enters the spatial light modulator 259 via the spherical mirrors 260-1 and 260-2 for modulation. The spatial light modulator 259 performs modulation by utilizing an orientation of a liquid crystal, and is arranged in such an orientation that modulates a phase of a linear polarized light (P-polarized light) in the direction parallel to the paper surface. This orientation coincides with the orientation of the polarization of the measurement beam 206.

Then, the measurement beam 206 passes through a polarizing plate 273, and enters the mirror of the X scanner 221 via the spherical mirrors 260-3 and 260-4. The polarizing plate 273 has a function of leading to the spatial light modulator 259 only the linear polarized light in the direction parallel to the paper surface out of the return beam 208. The X scanner 221, i.e., a resonance type scanner, scans the fundus with the measurement beam 206 in the direction parallel to the paper surface. The drive frequency of the X scanner 221 is about 7.9 kHz.

Then, the measurement beam 206 enters the mirror of the XY scanner 219 via the spherical mirrors 260-5 and 260-6. Although the XY scanner 219 is illustrated as one mirror, it is actually composed of two mirrors (a mirror for X scanning and a mirror for Y scanning) arranged closely to each other. The center of the measurement beam 206 is adjusted so as to coincide with the rotational center of the mirror of the XY scanner 219. The drive frequency of the XY scanner 219 is variable within a range of up to 500 Hz.

The spherical mirrors 260-7, 260-8, and 260-9 form an optical system having a function of scanning a retina 227 with the measurement beam 206 by using the vicinity of the cornea 226 as a fulcrum.

Although the beam diameter of the measurement beam 206 is 4 mm, the beam diameter may be increased to acquire a higher resolution tomographic image.

A motor-driven stage 217-2 is movable in the direction indicated by the arrows to enable adjusting and controlling the position of the accompanying spherical mirror 260-8. Similar to the motor-driven stage 217-1, the motor-driven stage 217-2 is controlled by the motor-driven stage drive driver 283.

The measurement beam 206 can be focused onto a predetermined layer of the retina 227 of the subject's eye 207 by adjusting the position of the spherical mirror 260-8, so that the observation can be performed. In the initial state, the position of the spherical mirror 260-8 is adjusted so that the measurement beam 206 enters the cornea 226 as a parallel beam.

The above configuration is also applicable to a case where the subject's eye 207 has a refractive error.

When the measurement beam 206 enters the subject's eye 207, it becomes the return beam 208 by the reflection and dispersion from the retina 227. The return beam 208 is led again to the optical coupler 231 and reaches the line sensor 239.

A part of return beam 208 is reflected by the movable beam splitter 261 and then led to the detector 238 via a lens 235-5. A light shielding plate 272 having a pinhole has a function of blocking unnecessary light which is not focused onto the retina 227 out of the return beam 208. The light shielding plate 272 is arranged at the focusing position of the lens 235-5 in a conjugated way. The diameter of the pinhole of the light shielding plate 272 is, for example, 50 μm. The detector 238 is, for example, an avalanche photo diode (APD) which is a high-speed high-sensitivity optical sensor.

A part of the return beam 108 split by the beam splitter 258 enters a wavefront sensor 255 which is a Shack-Hartmann wavefront sensor.

The spherical mirrors 260-1 to 260-9 are arranged so that the XY scanner 219, the X scanner 221, the cornea 226, the wavefront sensor 255, and the spatial light modulator 259 become optically conjugated. This configuration enables the wavefront sensor 255 to measure the aberration of the subject's eye 207, and enables the spatial light modulator 259 to correct the aberration of the subject's eye 207. Controlling the spatial light modulator 259 in real time based on the acquired aberration enables correcting the aberration occurring in the subject's eye 207 and acquiring a tomographic image having a higher lateral resolution.

[Configuration of Measurement System]

Configurations of measurement systems will be described below.

The ocular imaging apparatus 20 can acquire a tomographic image (OCT image) and a planar image (SLO image).

A tomographic image measurement system will be described below.

The returned beam 208 is multiplexed by the optical coupler 231. The multiplexed beam 242 is led to a transmission grating 241 via a single mode fiber 230-3 and a lens 235-2 to be dispersed into each wavelength, and then enters the line sensor 239 via a lens 235-3.

The line sensor 239 converts the light intensity into a voltage signal for each position (wavelength). A frame grabber 240 converts the voltage signal to a digital form. The personal computers 225 forms a tomographic image of the subject's eye 207 based on the digital signal.

In this case, the line sensor 239 has 1024 pixels to enable acquiring the light intensity for each wavelength (split by 1024) of the multiplexed beam 242.

A planar image measurement system will be described below.

A part of the return beam 208 is reflected by the movable beam splitter 261. After the light shielding plate 272 blocks unnecessary light, the reflected light of the return beam 208 reaches the detector 238 and the light intensity is converted into an electrical signal.

The personal computer 225 applies data processing in synchronization with scanning signals of the X scanner 221 and the XY scanner 219 to the acquired electrical signal to form a planar image.

Apart of the return beam 208 split by the beam splitter 258 enters the wavefront sensor 255 which measures the aberration of the return beam 208.

The personal computer 225 takes in the image signal acquired by the wavefront sensor 255 and calculates the aberration. The acquired aberration is represented by the Zernike polynomial to indicate the aberration of the subject's eye 207.

The Zernike polynomial includes a term of tilt (inclination), a term of defocus, a term of astigmatism, a term of coma, a term of trefoil, etc.

[OCT Image Acquiring Method]

A method for acquiring a tomographic image (OCT image) by the ocular imaging apparatus 20 will be described below with reference to FIGS. 4A to 4C.

The ocular imaging apparatus 20 controls the XY scanner 219, uses the X scanner 221 as a fixed mirror, and acquires an interference fringe by the line sensor 239 to enable acquiring a tomographic image of the retina 227. The ocular imaging apparatus 20 controls the movable beam splitter 261 so that the return beam 208 is not led to the detector 238. The X scanner 221 and the XY scanner 219 are controlled by the personal computer 225 via the optical scanner drive driver 282 in the driver unit 281. In this case, a method for acquiring a tomographic image of the retina 227 (on a plane parallel to the optical axis) will be described below.

Figure 4A:
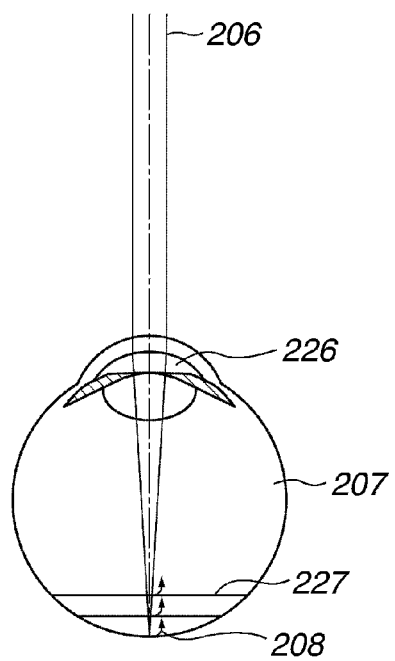
FIGS. 4A to 4C illustrate a method for acquiring an image performed by the ocular imaging apparatus according to the exemplary embodiment.

FIG. 4A schematically illustrates the subject's eye 207 under observation by the ocular imaging apparatus 20.

As illustrated in FIG. 4A, when the measurement beam 206 passes through the cornea 226 and enters the retina 227, it becomes the return beam 208 by the reflection and dispersion at various positions on the retina 227, and reaches the line sensor 239 accompanying time delays at respective positions.

In this case, since the light source 201 has a wide bandwidth and a short coherence length, when the optical path length of the reference beam path is approximately the same as the optical path length of the measurement beam path, the line sensor 239 can detect an interference fringe.

As described above, the line sensor 239 acquires an interference fringe of the spectral region on the wavelength axis.

Then, the ocular imaging apparatus 20 converts the interference fringe, that is information on the wavelength axis, into an interference fringe on the optical frequency axis in consideration of the characteristics of the line sensor 239 and the transmission grating 241.

The ocular imaging apparatus 20 further applies the inverse Fourier transform to the converted interference fringe on the optical frequency axis to acquire information about the depth direction.

Figure 4B:
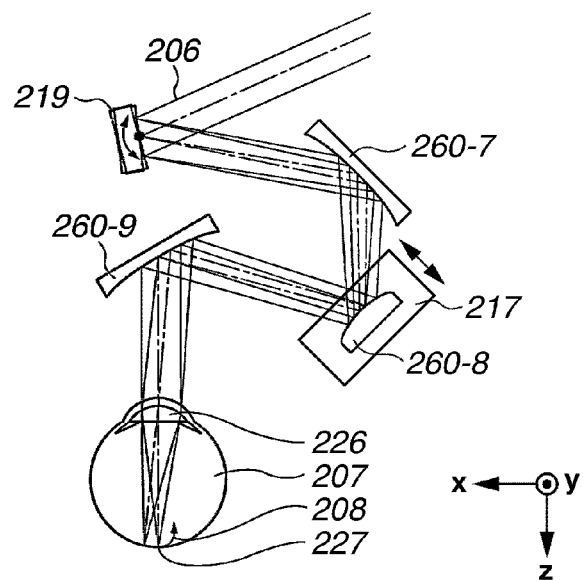

As illustrated in FIG. 4B, an interference fringe for each X-axis position can be acquired by detecting an interference fringe while driving the XY scanner 219, thus the information about the depth direction can be acquired for each X-axis position.

As a result, a two-dimensional distribution of the light intensity of the return beam 208 on the XZ plane, i.e., a tomographic image 232 (FIG. 4C), can be acquired.

As described above, the tomographic image 232 is formed by arranging the light intensity of the return beam 208 in array form. For example, the tomographic image 232 can be displayed by applying the light intensity to the gray scale. The length of the tomographic image 232 in the X direction is 700 µm.

Figure 4C:
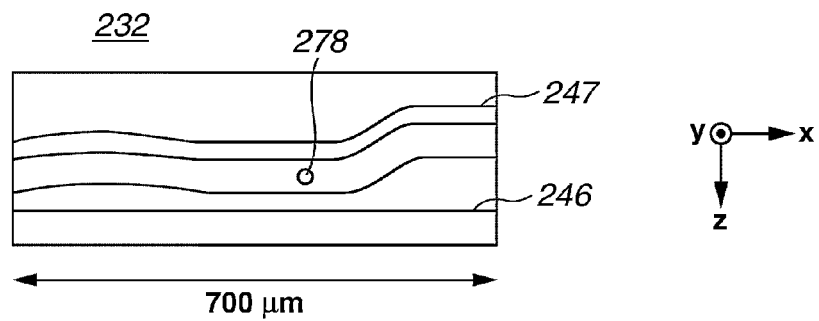

Referring to FIG. 4C, only the boundaries of the acquired tomographic image 232 are emphasized. The tomographic image 232 includes a retinal pigment epithelial layer 246, a nerve fiber layer 247, and a blood vessel 278.

[SLO Image Acquiring Method]

A method for acquiring a planar image (SLO image) by the ocular imaging apparatus 20 will be described below.

The ocular imaging apparatus 20 operates and controls the XY scanner 219 (only in the Y-axis direction) and the X scanner 221, fixes the X-axis direction of the XY scanner 219, and acquires the light intensity of the return beam 208 by the detector 238, thus acquiring a planar image of the retina 227. The X scanner 221 and the XY scanner 219 are controlled by the personal computer 225 via the optical scanner drive driver 282 in the driver unit 281.

The ocular imaging apparatus 20 further controls the spatial light modulator 259 with use of the aberration of the subject's eye 207 measured by the wavefront sensor 255 to enable acquiring a planar image while correcting the aberration caused in the subject's eye 207. The ocular imaging apparatus 20 further controls the spatial light modulator 259 in real time to enable acquiring the planar image.

As described above, the SLO employing the adaptive optics can acquire an image of capillaries, nerve fibers, and visual cells around a macula or an optic disc which are minuter than blood vessels targeted by a conventional Fourier domain OCT and a fundus camera.

Functions of each block constituting the image processing apparatus 10 will be described below in association with the processing performed by the image processing apparatus 10 illustrated in the flowchart in FIG. 5.

[Step S510]

In step S510, the SLO image acquisition unit 100 requests the ocular imaging apparatus 20 to acquire an SLO image (still image or moving image). When necessary, the volume image acquisition unit 110 requests the ocular imaging apparatus 20 to acquire an ocular volume image. In the present exemplary embodiment, the ocular imaging apparatus 20 inputs an SLO moving image M1 (frame number i=1, 2, . . . , N) illustrated in FIG. 7A and an ocular volume image illustrated in FIG. 6A. For the SLO moving image M1, the ocular imaging apparatus 20 sets a focusing position F1 in the vicinity of the boundary between an inner segment and an outer segment of the visual cell, as illustrated in FIG. 6A.

Figure 6A:
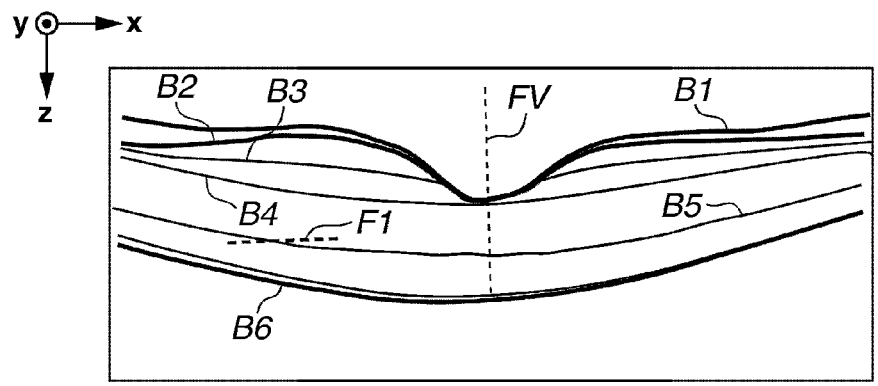
FIGS. 6A to 6D illustrate image processing according to the exemplary embodiment.
Figure 6B:
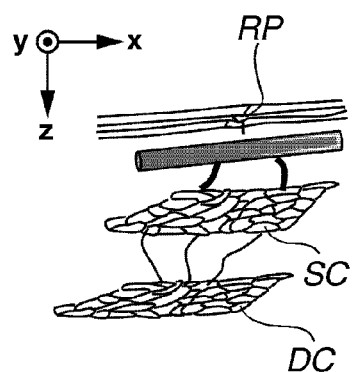
Figure 6C:
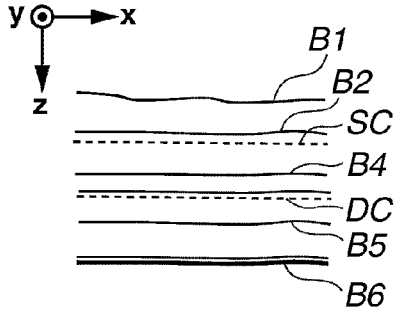
Figure 6D:
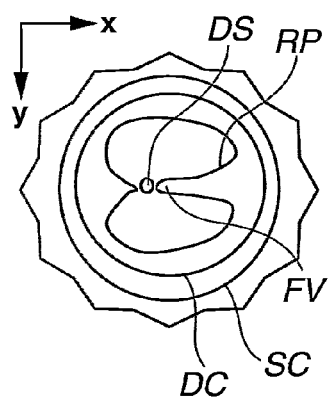

FIGS. 6A to 6D will be described below. FIG. 6A illustrates a focusing position to be set in the present exemplary embodiment. FIG. 6B illustrates surface capillaries (SC) and deep capillaries (DC) constituting retinal blood vessels and capillaries of the fundus. FIG. 6C illustrates depth positions of the surface capillaries (SC) and the deep capillaries (DC) in a retinal tomographic image. FIG. 6D illustrates a range in the fundus where radial peripapillary capillaries (RPC), the surface capillaries, and the deep capillaries exist.

Figure 7A:
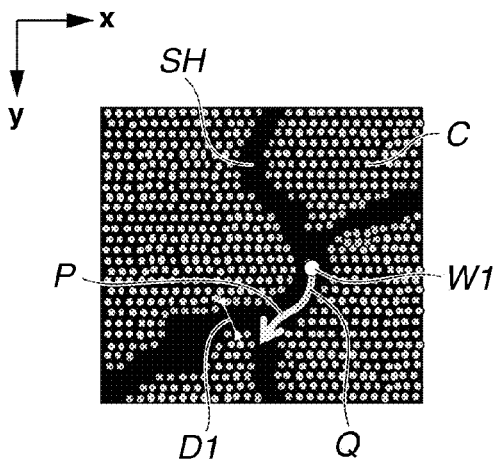
FIGS. 7A to 7C illustrate blood flow analysis processing according to the exemplary embodiment.
Figure 7B:
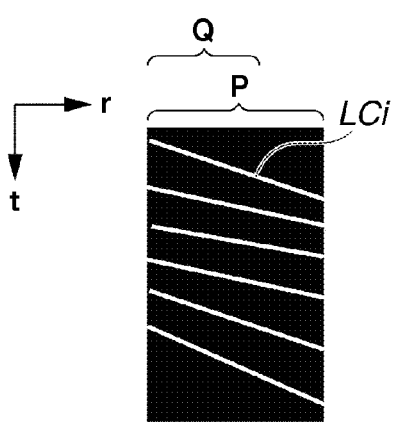
Figure 7C:
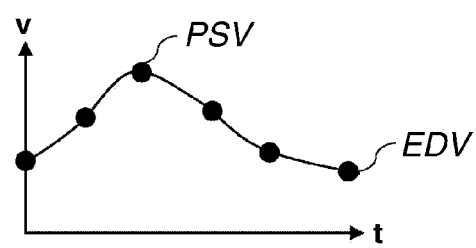

FIG. 7A illustrates an example AO-SLO moving image acquired when the focusing position is set in the vicinity of the visual cell inner segment/outer segment boundary. FIG. 7B illustrates an example time-space image of the SLO moving image M1 which can be taken along a path P on the blood vessel. FIG. 7C illustrates an example graph of the blood flow velocity.

The ocular imaging apparatus 20 acquires an SLO moving image and an ocular volume image in response to the acquisition request and transmits these images. The SLO image acquisition unit 100 thus receives the SLO moving image M1 from the ocular imaging apparatus 20 via a local area network (LAN) 30, and stores the received SLO moving image M1 in the storage unit 120.

[Step S520]

In step S520, based on the image acquired in step S510, the structure identification unit 130 identifies retinal blood vessels as an ocular feature. In the present exemplary embodiment, the ocular imaging apparatus 20 acquires the SLO moving image and the ocular volume image. Thus, the structure identification unit 130 acquires data of a retinal blood vessel shadow SH and high luminance blood cell components W1 acquired from the SLO moving image M1 as illustrated in FIG. 7A as the ocular features. As ocular features, the structure identification unit 130 further extracts an inner limiting membrane B1, a nerve fiber layer boundary B2, an inner plexiform layer boundary B4, a visual cell inner segment/outer segment boundary B5, a retinal pigment epithelium outer boundary B6, the surface capillaries (SC), and the deep capillaries (DC) from the ocular volume image. The structure identification unit 130 further stores each of the acquired ocular feature data pieces in the storage unit 120, and transmits it to the data server 40 as required.

Specific procedures for acquiring the ocular features will be described below.

Considering a processing target ocular volume image as a set of two-dimensional tomographic images (B scan images), the structure identification unit 130 applies the following processing to each two-dimensional tomographic image.

First of all, the structure identification unit 130 applies smoothing processing to a target two-dimensional tomographic image to remove noise components. Then, the structure identification unit 130 detects edge components from the two-dimensional tomographic image and, based on their connectivity, extracts some line segments as layer boundary candidates. Then, the structure identification unit 130 recognizes the top, second, and third line segments from among the layer boundary candidates as the inner limiting membrane B1, the nerve fiber layer boundary B2, and the inner plexiform layer boundary B4, respectively. The structure identification unit 130 further selects a line segment having a maximum contrast existing on the outer layer side of the inner limiting membrane B1 (the side having a larger z coordinate value in FIG. 6A) as the visual cell inner segment/outer segment boundary B5. The structure identification unit 130 further selects a bottom line segment from among the layer boundary candidates as the retinal pigment epithelial layer outer boundary B6.

The structure identification unit 130 may further apply a deformable model based on Snakes and the level set method by using these line segments as initial values to perform precision extraction. The structure identification unit 130 may further detect layer boundaries by the graph cut method. Processing for layer boundary detection based on the deformable model or the graph cut method may be three-dimensionally applied to the volume image or two-dimensionally applied to each two-dimensional tomographic image. Any method for detecting a layer boundary may be used as long as it can detect layer boundaries from an ocular tomographic image.

Then, the structure identification unit 130 detects the surface capillary area SC and the deep capillary area DC from the ocular volume image. More specifically, the structure identification unit 130 generates a projection image in the depth direction only for a range from the nerve fiber layer boundary B2 to the inner plexiform layer boundary B4, and detects the surface capillary area SC on the projection image with use of a known line detection filter. Similarly, the structure identification unit 130 generates a projection image in the depth direction only for a range from the inner plexiform layer boundary B4 to the visual cell inner segment/outer segment boundary B5, and detects the deep capillary area DC on the projection image with use of the known line detection filter.

Subsequently, the structure identification unit 130 detects the retinal blood vessel shadow area SH from the SLO moving image M1. More specifically, the structure identification unit 130 performs differential processing between contiguous frames of the SLO moving image M1 to investigate pixel values in the frame direction at each x-y position, thus obtaining a standard deviation of the pixel values. The structure identification unit 130 detects an area having the standard deviation equal to or greater than a threshold value T1 as the blood vessel shadow area SH.

The structure identification unit 130 further detects the high luminance blood cell components from the SLO moving image M1 with use of arbitrary known image processing method. In the present exemplary embodiment, the structure identification unit 130 acquires a moving locus of the high luminance blood cell components W1 by the following procedures:

(i) generating a time-space image, and
(ii) detecting linear areas on the time-space image.

In the procedure (i), as illustrated in FIG. 7B, the structure identification unit 130 generates a time-space image having the horizontal axis assigned a position r and the vertical axis assigned a time t at a blood vessel center line P acquired by thinning the lines of an area where retinal blood vessels exist, i.e., an area having the same x-y coordinates as the retinal blood vessel shadow area SH. The time-space image is equivalent to a curved cross sectional image of the SLO moving image M1 taken along the path P. The time t is acquired by dividing a frame number i of the SLO moving image M1 by a frame rate k [1/sec]. The time-space image includes a plurality of high luminance linear components LCi which indicate the blood cell components' moving distance.

In the procedure (ii), the structure identification unit 130 detects high luminance linear areas LCi on the time-space image. In this case, the linear areas LCi are detected after emphasizing the lines with use of arbitrary known line emphasis filter and converting the image into binary data based on a threshold value Tt.

[Step S530]

In step S530, the measurement data acquisition unit 140 measures blood flow dynamic states based on the SLO moving image M1, the ocular volume image, and the ocular features acquired in step S520 and acquires blood flow information such as the blood flow velocity and blood flow rate. Specific measurement processing will be described in detail below.

Although, in the present exemplary embodiment, the image processing apparatus 10 directly performs the measurement processing, the processing is not limited thereto. For example, an image processing apparatus may be separately provided, and the measurement data acquisition unit 140 may receive data measured by the image processing apparatus.

[Step S540]

In step S540, the determination unit 160 determines the following display-related parameters based on the SLO moving image M1, the ocular volume image, the ocular features, and the measurement data acquired in step S530:

(i) Blood vessel diameter sizes to be handled as the same group when making statistics on measurement values, (ii) a range of moving image frames to be used for making the statistics and/or comparison of measurement results (e.g., number of heartbeat cycles or a phase range from one certain phase to another), (iii) whether the depth position of capillaries is to be distinguished, and the depth position when distinguished, (iv) statistical value type, and (v) division of local areas used for comparison.

Specific settings of setting parameters will be described in detail below.

[Step S550]

In step S550, the display control unit 170 generates image data for displaying the ocular image acquired in step S510 and measurement data of the blood flow information acquired by the measurement data acquisition unit 140 in step S530 based on the display-related parameters set by the determination unit 160, and instructs the display unit 190 to display a relevant image. Contents of the image data will be described in detail below.

[Step S560]

In step S560, the instruction acquisition unit 180 acquires from external an instruction about whether the display contents of the measurement data output by the display control unit 170 in step S550 is to be stored in the data server 40. This instruction is input by an operator, for example, via the operation unit 150. When the storage of the display contents is instructed (YES in step S560), the processing proceeds to step S570. Otherwise, when the storage of the display contents is not instructed (NO in step S560), the processing proceeds to step S580.

[Step S570]

In step S570, the display control unit 170 associates a test date, information for identifying the subject's eye, and the measurement results with each other and transmits the associated information to the data server 40.

[Step S580]

In step S580, the instruction acquisition unit 180 acquires from external an instruction about whether the SLO image measurement data display processing by the image processing apparatus 10 is to be ended. This instruction is input by the operator via the operation unit 150. When an instruction for ending the display processing is acquired (YES instep S580), the display processing is ended. Otherwise, when an instruction for continuing the display processing is acquired (NO in step S580), the processing returns to step S510, and the image processing apparatus 10 performs processing for the next subject's eye (or reprocessing for the same subject's eye).

Figure 8A:
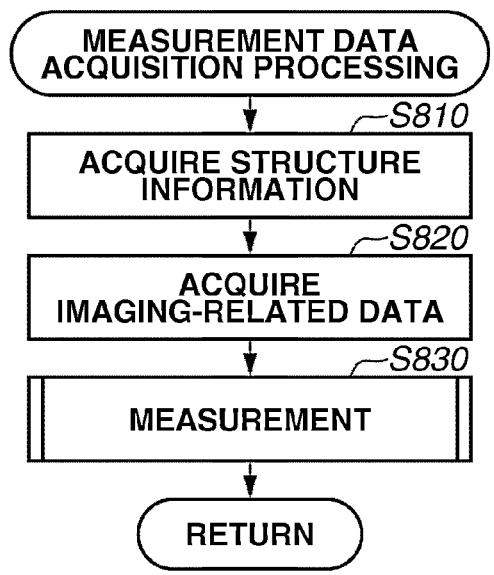
FIGS. 8A and 8B are flowcharts illustrating detailed processing performed in step S530 in FIG. 5 according to the exemplary embodiment.

The processing performed in step S530 will be described in detail below with reference to FIG. 8A.

[Step S810]

In step S810, the measurement data acquisition unit 140 acquires the ocular features acquired in step S520. More specifically, the measurement data acquisition unit 140 acquires the retinal blood vessel shadow area SH and the high luminance blood cell components W1 on the SLO moving image M1, and the inner limiting membrane B1, the nerve fiber layer boundary B2, the inner plexiform layer boundary B4, the visual cell inner segment/outer segment boundary B5, the retinal pigment epithelial layer outer boundary B6, the surface capillaries SC, and the deep capillaries DC acquired from the ocular volume image.

[Step S820]

In step S820, the measurement data acquisition unit 140 acquires as imaging-related data from the data server 40 pulse wave data and fixation target position data used when capturing the SLO moving image M1. The pulse wave data is acquired simultaneously when capturing the SLO moving image M1. The pulse wave data is used for associating each frame of the SLO moving image M1 with the heartbeat phase.

[Step S830]

In step S830, the measurement data acquisition unit 140 acquires measurement data for blood flow dynamic states with use of the ocular image acquired in step S510, the ocular features acquired in step S520, and the imaging-related data acquired in step S830. In the present exemplary embodiment, the measurement data acquisition unit 140 acquires the blood flow velocity (blood cell components' moving velocity) and the blood flow rate (product of the blood vessel cross section and the blood flow velocity) as a blood flow dynamic state.

Figure 8B:
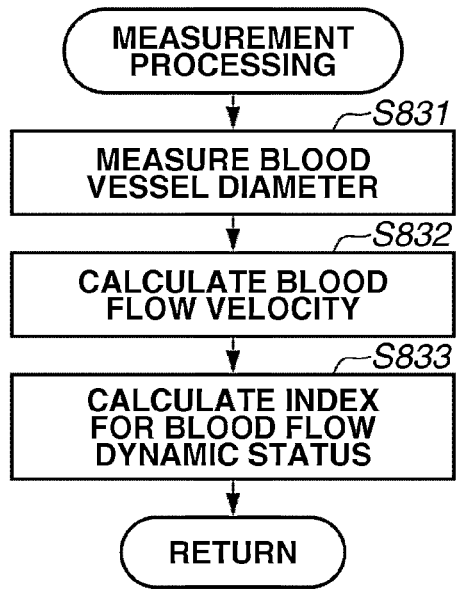

The processing performed in step S830 will be described in detail below with reference to FIG. 8B.

[Step S831]

In step S831, the measurement data acquisition unit 140 measures the blood vessel diameter in the retinal blood vessel shadow area SH acquired by the structure identification unit 130. More specifically, the measurement data acquisition unit 140 examines luminance values in the direction perpendicular to the blood vessel center line P, as illustrated in FIG. 7A, at each position Pi of the blood vessel center line P acquired by thinning the lines of the retinal blood vessel area SH. The measurement data acquisition unit 140 recognizes a distance range where the luminance value is equal to or greater than a threshold value T3 as a blood vessel diameter D1.

[Step S832]

In step S832, the measurement data acquisition unit 140 calculates a blood flow velocity v based on the linear areas LCi detected on the time-space image. More specifically, the measurement data acquisition unit 140 detects the linear area LCi as a straight line by using the Hough transform, and calculates the blood flow velocity v based on an angle and a distance of the straight line from the coordinate origin. The method for detecting a line is not limited thereto, and may be arbitrary known methods.

On the time-space image, the horizontal axis indicates a position r [mm] on the blood vessel, and the vertical axis thereof indicates the time t [sec] during which blood cell components pass through the position r. For example, when r=0, plotting data with the time t assigned to the horizontal axis and the blood flow velocity v assigned to the vertical axis enables obtaining a graph of the blood flow velocity as illustrated in FIG. 7C.

[Step S833]

In step S833, the measurement data acquisition unit 140 calculates a blood flow dynamic state index based on the values of the blood vessel diameter calculated in step S831 and the blood flow velocity v calculated in step S832. In the present exemplary embodiment, the measurement data acquisition unit 140 calculates the blood flow rate (Flow: FL) by the following formula as the blood flow dynamic state index.

$$\text{Blood flow rate } FL[\text{ml/min}] = 0.06 \times \text{Blood flow velocity [mm/sec]} \times \text{Blood vessel cross section [mm}^2]$$

In this case, the measurement data acquisition unit 140 uses the value of the blood vessel cross section calculated based on the value of the blood vessel diameter (assuming that the shape of the blood vessel cross section is a circle). Accordingly, an amount of blood supply per unit time can be quantitatively evaluated at a measuring position.

The blood flow dynamic state index is not limited to the above value. For example, a pulsatility index (PI) and a resistance index (RI) may be calculated by the following formulas:

Pulsatility index $PI=(PSV-EDV)/Va$

Resistance index $RI=(PSV-EDV)/PSV$ where PSV indicates the maximum blood flow velocity in the contraction phase, EDV indicates the blood flow velocity in the end-diastole phase, and Va indicates an average blood flow velocity. The pulsation cycle, and positions of the contraction phase and the end-diastole phase are determined based on the pulse wave data.

The above-described indices enable quantitative evaluation of the ease of blood flow at the measuring position.

The processing performed in step S540 will be described in detail below with reference to FIG. 9.

[Step S910]

In step S910, the blood vessel feature determination unit 1601 determines types and ranges of relevant values of the blood vessel features which are distinguished when making statistics on measurement values. In the present exemplary embodiment, the blood vessel feature determination unit 1601 determines to use the blood vessel diameter as a blood vessel feature and to classify the distinguishable ranges of the blood vessel diameter into three groups, i.e., 5 to 10 μm, 10 to 15 μm, and 15 to 20 μm, when making statistics on the measurement values.

The distinguishable ranges of the blood vessel diameter are not limited thereto, and may be any values.

[Step S920]

In step S920, the pulse wave synchronization setting unit 1602 determines a range of frames (frame number list) to be used when applying statistical processing to dynamic state measurement data for the SLO moving image M1 acquired through repetitive image capturing over a fixed time period.

Blood consists of about 1% of leukocytes which are visibly counted on the SLO moving image. A limited number of leukocytes can be detected within an imaging time. (Blood consists of about 55% of plasma component and about 45% of blood cell components including about 3% of leukocytes.) Accordingly, there are a limited number of straight lines LCi indicating the moving locus of leukocytes detectable on the time-space image, resulting in insufficient number of points in a blood flow velocity graph as illustrated in FIG. 7A when performing in-depth analysis of variation in blood flow velocity.

Figure 10:
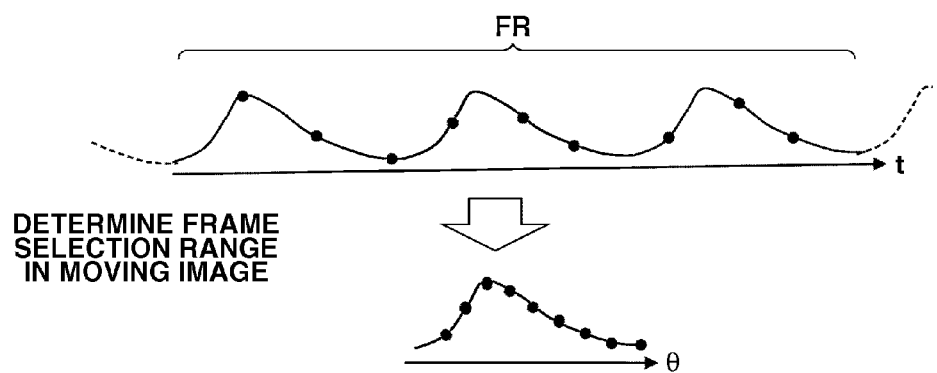
FIG. 10 illustrates processing for measuring blood flow fluctuations according to the exemplary embodiment.

To solve this issue, a phase in the heartbeat cycle to which each frame of the moving image corresponds is obtained by using the pulse wave data and, according to values of the obtained phase, blood flow velocity data for a plurality of the heartbeat cycles is collectively displayed in a form of blood flow velocity wave for one heartbeat cycle as illustrated in FIG. 10. The phase may be represented by continuous values or discrete values. However, when the phase is represented by discrete values, it is necessary to specify a quantization level (number of sections into which one heartbeat cycle is divided). When the phase is represented by discrete values, measurement values are averaged within a local section resulting in a smooth blood flow velocity waveform.

In the present exemplary embodiment, the pulse wave synchronization setting unit 1602 determines
(i) how many sections (the number of sections IN) is one heartbeat cycle divided into, and
(ii) how many heartbeat cycles (the number of heartbeat cycles PN) are used from the display target SLO moving image as a frame for statistical processing and comparison of the statistical values.

The item (i), i.e., the number of divisions (IN), is input in advance from the instruction acquisition unit 180 according to a waveform minuteness desired by a user.

For the item (ii), i.e., the number of heartbeat cycles (PN), the pulse wave synchronization setting unit 1602 performs the following processing referring to each frame of the display target SLO moving image:
(ii-a) calculate an image quality evaluation index (signal-to-noise (S/N) ratio in the present exemplary embodiment) for each frame, and
(ii-b) perform position adjustment between frames by a known method to calculate translational movement parameters for the entire image between frames.

The above-described pieces of processing (ii-a) and (ii-b) detect frames having an image quality index less than a threshold value Tq because of blinking, and frames having an inter-frame positional deviation equal to or greater than a threshold value Ts because of involuntary eye movement during visual-fixation; and sets the number of heartbeat cycles Pfr for a maximum frame range FR not including the detected frames as the number of heartbeat cycles (PN).

However, when the number of heartbeat cycles Pfr differs between comparison target SLO moving images, a minimum number of the heartbeat cycles Pfr between comparison target areas is set as the number of heartbeat cycles (PN).

[Step S930]

In step S930, the blood vessel depth position determination unit 1603 specifies
(i) whether to display the depth positions distinctively, and
(ii) each depth position when distinctively displayed.

As illustrated in FIG. 6D, the fundus includes three different areas, an area where radial peripapillary capillaries (RPC), surface capillaries, and deep capillaries exist (an area enclosed by a line RP), an area where surface capillaries and deep capillaries exist (an area enclosed by a line DC), and an area where only surface capillaries exist (an area formed by subtracting the deep capillary area DC from the surface capillary area SC).

In the present exemplary embodiment, the macular portion is under observation, and to comparatively display the amount of blood flow supplied to layers constituting the retina (a nerve fiber layer, a ganglion cell layer, an inner granular layer, and an outer plexiform layer), the blood vessel depth position determination unit 1603
(i) distinguishes the depth position, and
(ii) specifies the position of surface capillaries SC (slightly on the outer layer side of the nerve fiber layer boundary B2) and the position of deep capillaries DC (slightly on the outer layer side of an inner granular layer (not illustrated)).

In the present exemplary embodiment, information about the fixation target position when capturing the SLO moving image M1 which is acquired from the data server 40 in advance is used as a method for obtaining a positional relation between the ocular volume image and the SLO moving image M1.

[Step S940]

In step S940, the statistical value determination unit 1604 determines types of statistical values used for statistical processing for measurement data. In the present exemplary embodiment, the statistical value determination unit 1604 obtains the average value, maximum value, and minimum value of measurement values within local areas. However, statistical values are not limited thereto, and may be any values.

[Step S950]

In step S950, the comparison target determination unit 1605 determines comparison target areas at the time of statistical value comparison.

The comparison target areas include
(i) a plurality of local areas on one eye,
(ii) identical areas on right and left eyes,
(iii) an identical area on one eye captured on different dates, and
(iv) an identical area on one eye of different subjects.

In the present exemplary embodiment, the comparison target determination unit 1605 performs statistical data comparison between (i) a plurality of local areas of one eye.

Although any area can be set as a local area, a chart as illustrated in FIG. 11A is used. In this chart, the SLO image is divided into four (top, bottom, left, and right) areas centering on fovea centralis, and each division area is further divided into two areas, that is an area near the fovea centralis and an area far therefrom. In the present exemplary embodiment, measurement values are not input for a local area directly under the fovea centralis since this local area is an avascular area.

The processing performed in step S550 will be described in detail below with reference to FIGS. 11A to 11C.

First of all, the image processing unit 10 comparatively displays the blood flow velocity between local areas around the macular portion. As illustrated in FIG. 11A, the image processing unit 10 provides the above-described chart for each vessel diameter, and displays values of the average blood flow velocity in each local area on the chart. However, it is not necessary to provide a separate chart for each vessel diameter. For example, as illustrated in FIG. 11B, values may be displayed in different colors on the same chart.

Then, as illustrated in FIG. 11C, the image processing unit 10 distinctively displays the amount of blood per unit time supplied to layers in the vicinity of surface capillaries of the macular portion (the nerve fiber layer and the ganglion cell layer), and the amount of blood per unit time supplied to layers in the vicinity of deep capillaries (the inner granular layer and the outer plexiform layer). The image processing unit 10 may further display a differential chart for the two charts in FIG. 11C. Accordingly, comparative display of the amount of blood per unit time supplied by the surface and deep capillaries can be realized.

According to the above-described configuration, the image processing apparatus 10 measures as blood flow dynamic states the blood flow velocity and the blood flow rate based on the SLO moving image M1 capturing capillaries around the fovea centralis, and, in consideration of the blood vessel diameter, pulsation cycle, and depth position of capillaries, comparatively displays statistical values related to the blood flow dynamic states for each local area.

In the case of blood flow dynamic state such as the blood flow velocity, since a range of normal blood flow velocity differs for each blood vessel diameter, it is necessary to perform statistical processing for each vessel diameter. Since the blood flow velocity is subject to the influence of pulsation, it is necessary, when performing statistical value calculation and comparison, to select pulsation cycles in the same phase. Further, since capillaries are classified into surface capillaries and deep capillaries as illustrated in FIG. 7B, it is necessary, when making statistics, to distinguish these two different capillaries to correctly grasp the blood flow distribution of capillaries.

The above-described configuration enables more exactly displaying the ocular cells' dynamic states reflecting the normal moving velocity value and pulsation cycle of ocular cells, and depth positions where a blood vessel exists.

In a second exemplary embodiment, instead of comparatively displaying measurement data for blood flow dynamic states between local areas around the macular portion as in the first exemplary embodiment, measurement data for blood flow dynamic states around optic disc is comparatively displayed between right and left eyes or aging data.

The function block diagram of the image processing apparatus 10 according to the present exemplary embodiment is similar to that in FIG. 1, and the flow of the image processing according to the present exemplary embodiment is as illustrated in FIG. 5. Except for steps S520, S540, and S550, the processing according to the present exemplary embodiment is similar to that in the first exemplary embodiment. In the present exemplary embodiment, therefore, duplicated descriptions of the processing in steps S510, S530, S560, S570, and S580 will be omitted.

[Step S520]

In step S520, the structure identification unit 130 acquires ocular features from the image acquired in step S510. In the present exemplary embodiment, the ocular imaging apparatus 20 acquires the SLO moving image and the ocular volume image. Thus, the structure identification unit 130 acquires data of a retinal blood vessel shadow SH and high luminance blood cell components W1 acquired from the SLO moving image M1 as illustrated in FIG. 7A as the ocular features.

As the ocular features, the structure identification unit 130 further extracts an inner limiting membrane B1, a nerve fiber layer boundary B2, an inner plexiform layer boundary B4, a visual cell inner segment/outer segment boundary B5, a retinal pigment epithelium outer boundary B6, the radial peripapillary capillaries RPC, the surface capillaries SC, and the deep capillaries DC from the ocular volume image.

The structure identification unit 130 further stores each of the acquired ocular feature data pieces in the storage unit 120, and transmits it to the data server 40 as required.

Specific procedures for acquiring the ocular features will be described below.

The processing for detecting layer boundaries, the surface capillary area SC, and the deep capillary area DC from the ocular volume image, and the processing for detecting the retinal blood vessel shadow area SH from the SLO moving image M1 are similar to those in the first exemplary embodiment, and duplicated descriptions will be omitted.

Then, the structure identification unit 130 detects the radial peripapillary capillaries RPC from the ocular volume image. More specifically, the structure identification unit 130 generates a projection image in the depth direction only for a range from the inner limiting membrane B1 to the nerve fiber layer boundary B2, and detects the radial peripapillary capillaries RPC area on the projection image by a known line detection filter.

The method for acquiring ocular features is not limited thereto. For example, ocular feature types instructed by the instruction acquisition unit 180 may be acquired.

The structure identification unit 130 further stores the detected ocular feature data in the storage unit 120, and transmits it to the data server 40 as required.

[Step S540]

In step S540, the determination unit 160 determines the following display-related parameters based on the SLO moving image M1, the ocular volume image, the ocular features, and the measurement data acquired in step S530:
(i) Blood vessel diameter sizes to be handled as the same group when making statistics on measurement values,
(ii) a range of moving image frames to be used for making the statistics and/or comparison of measurement results (e.g., number of heartbeat cycles or a phase range from one certain phase to another),
(iii) whether the depth position of capillaries is to be distinguished, and the depth position when distinguished,
(iv) statistical value type, and
(v) division of local areas used for comparison.

The processing performed in step S540 will be described in detail below with reference to FIGS. 6A to 6D and FIG. 9.
[Step S910]
In step S910, the blood vessel feature determination unit 1601 determines types and ranges of relevant values of the blood vessel features which are distinguished when making statistics on measurement values. In the present exemplary embodiment, the blood vessel feature determination unit 1601 determines to use the blood vessel diameter as a blood vessel feature and to classify the distinguishable ranges of the blood vessel diameter into three groups, i.e., 5 to 10 µm, 10 to 15 µm, and 15 to 20 µm, when making statistics on the measurement values.

The distinguishable ranges of the blood vessel diameter are not limited thereto, and may be any values.
[Step S920]
In step S920, the pulse wave synchronization setting unit 1602 determines a range of frames (frame number list) to be used when applying statistical processing to dynamic state measurement data for the SLO moving image M1.

In the present exemplary embodiment, the pulse wave synchronization setting unit 1602 determines
(i) how many sections (the number of sections IN) is one heartbeat cycle divided into, and
(ii) how many heartbeat cycles (the number of heartbeat cycles PN) are used from the display target SLO moving image as a frame for statistical processing and comparison of the statistical values.

This processing is similar to that in the first exemplary embodiment, and duplicated descriptions will be omitted.
[Step S930]
In step S930, the blood vessel depth position determination unit 1603 specifies
(i) whether to display the depth positions distinctively, and
(ii) each depth position when distinctively displayed.

As illustrated in FIG. 6D, the fundus includes three different areas, an area where radial peripapillary capillaries (RPC), surface capillaries, and deep capillaries exist (an area enclosed by a line RP), an area where surface capillaries and deep capillaries exist (an area enclosed by a line DC), and an area where only surface capillaries exist (an area formed by subtracting the deep capillary area DC from the surface capillary area SC).

In the present exemplary embodiment, the optic disc is under observation, and to comparatively display the amount of blood flow supplied to layers constituting the retina (a nerve fiber layer, a ganglion cell layer, an inner granular layer, and an outer plexiform layer), the blood vessel depth position determination unit 1603
(i) distinguishes the depth position, and
(ii) specifies the position of radial peripapillary capillaries RPC (slightly on the outer layer side of the inner limiting membrane B1), the position of surface capillaries SC (slightly on the outer layer side of the nerve fiber layer boundary B2), and the position of deep capillaries DC (slightly on the outer layer side of the inner granular layer (not illustrated)).

In the present exemplary embodiment, information about the fixation target position when capturing the SLO moving image M1 which is acquired from the data server 40 in advance is used as a method for obtaining a positional relation between the ocular volume image and the SLO moving image M1.
[Step S940]
In step S940, the statistical value determination unit 1604 determines types of statistical values used for statistical processing for measurement data. In the present exemplary embodiment, the statistical value determination unit 1604 selects "Deviation" which indicates the deviation from the average value, the maximum value, the minimum value, and the normal value of the measurement values for each local area, and "Significance" which indicates the specificity of the measurement values when an identical portion is measured for different subjects.
[Step S950]
In step S950, the comparison target determination unit 1605 determines comparison target areas at the time of statistical value comparison. In the present exemplary embodiment, the comparison target determination unit 1605 uses the following areas as the comparison target.
(i) a plurality of local areas on one eye,
(ii) identical areas on right and left eyes, and
(iii) an identical area on one eye captured on different dates.

Figure 12C:
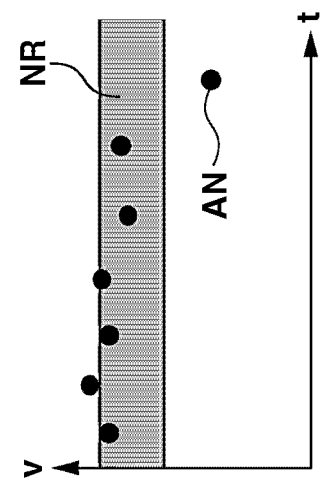
FIGS. 12A to 12C illustrate the contents of other measurement data displayed by the display control unit.
Figure 12B:
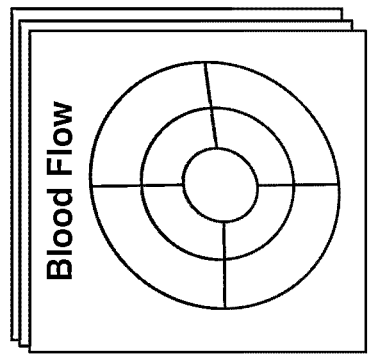
Figure 12A:
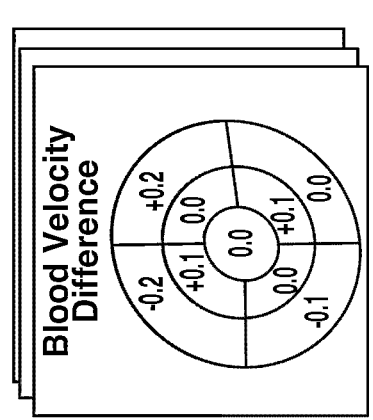

In the present exemplary embodiment, local areas are set with use of (i) a plurality of local areas on one eye and (ii) identical areas on right and left eyes, as illustrated in FIG. 12A. An area where a blood vessel lesion (coarctation or lump) was detected by the structure identification unit 130 in the SLO moving image captured in the past is set as the local area for (iii) an identical area on one eye captured on different dates.

Any known image processing method can be used to detect a blood vessel lesion. However, in the present exemplary embodiment, an area having a blood vessel diameter (when measured along the center line of the blood vessel after blood vessel extraction) less than a certain value is recognized as the coarctation, and an area having a blood vessel diameter equal to or greater than the certain value is recognized as a lump.

The method for setting local areas is not limited thereto. For example, the image may be divided into two local areas, i.e., upper and lower semicircles.
[Step S550]
In step S550, the display control unit 170 controls the display contents regarding the ocular image acquired in step S510 and the measurement data acquired by the measurement data acquisition unit 140 in step S530 based on the display-related parameters set by the determination unit 160.

More specifically, the image processing unit 10 displays a difference in the blood flow velocity between identical local areas (around optic disc) on the right and left eyes. The image processing unit 10 provides a chart as illustrated in FIG. 12A for each vessel diameter, and displays a difference in the average blood flow velocity in each local area between the right and left eyes. However, it is not necessary to provide a separate chart for each vessel diameter. For example, values may be displayed in different colors on the same chart.

Then, as illustrated in FIG. 12B, the image processing unit 10 distinctively displays the amount of blood per unit time supplied to layers in the vicinity of the radial peripapillary capillaries RPC of the optic disc (the nerve fiber layer), the amount of blood per unit time supplied to layers in the vicinity of the surface capillaries (the ganglion cell layer), and the amount of blood per unit time supplied to layers in the vicinity of the deep capillaries (the inner granular layer and the outer plexiform layer). The image processing apparatus 10 may further display a difference chart for any two charts out of the three different charts in FIG. 12B. Accordingly, comparative display of the amount of blood per unit time supplied by the three different capillaries around the optic disc can be realized.

As illustrated in FIG. 12C, the image processing apparatus 10 displays aging data for blood flow dynamic state measurement values (blood flow velocity) acquired at the optic disc local areas (or measuring points) set in step S950 on different dates. In the present exemplary embodiment, the image processing apparatus 10 displays the aging data related to the blood flow velocity in graph form as illustrated in FIG. 12C.

Assuming that the average value of past blood flow velocity values of the subject (solid line in FIG. 12C) as a normal value, the image processing apparatus 10 further recognizes aging data AN having a blood flow velocity less than a value lower than the normal value (dotted line in FIG. 12C) by a fixed ratio (5% in the present exemplary embodiment) as an abnormal value, and displays a relevant warning (in red). The method for displaying aging data is not limited thereto, and may be any method. The method for displaying a warning is not limited thereto neither, and may be any known method.

According to the above-described configuration, the image processing apparatus 10 measures as blood flow dynamic states the blood flow velocity and the blood flow rate based on the SLO moving image capturing capillaries around the optic disc. Further, in consideration of the blood vessel diameter, pulsation cycle, and depth position of capillaries, the image processing apparatus 10 comparatively displays statistical values related to blood flow dynamic states for right and left eyes or time series data.

Accordingly, the above-described configuration enables more exactly displaying the ocular cells' dynamic states reflecting the normal moving velocity value and pulsation cycle of ocular cells, and depth positions where a blood vessel exists.

In a third exemplary embodiment, when the image processing apparatus 10 determines an abnormal blood flow in a blood vessel having a certain diameter or a certain depth, the display control unit 144 displays a blood flow chart by emphasizing the values indicating the abnormal blood flow. The hardware configuration and processing flow are similar to those in the above-described exemplary embodiments, and duplicated descriptions will be omitted.

The data server 40 is used together with the image processing apparatus 10. The data server 40 stores measurement values measured by the measurement data acquisition unit 140 of the image processing apparatus 10 and image data generated by the display control unit 170 thereof in association with image capturing conditions and patient information. Information about the depth and abnormality for each blood vessel diameter is attached to the patient information by a medical doctor. The determination unit 150 compares blood flow information of a display target subject with blood flow information stored in the data server 40 and determines that a value deviated from the normal value by a predetermined threshold value or more is abnormal.

The display control unit 144 displays such abnormal values with emphasis than other information. For example, for each of the above-described local areas, if an abnormal blood flow velocity or abnormal blood flow rate is found at a certain depth, the display control unit 144 generates image data with which such abnormal values have different display form, for example, larger character sizes, different colors, blinking, different field colors, etc. The display control unit 144 displays the generated image data on the display unit 190.

In another example, the display control unit 144 may display a blood flow chart including values determined to be abnormal in preference to other blood vessel charts. For example, when a blood flow chart is generated by depth, the display control unit 144 displays a blood flow chart including abnormal values in a larger size than other blood flow charts, or displays only the blood flow chart including abnormal values and displays other charts in response to user selection. This display operation enables an examiner such as a medical doctor to promptly recognize an abnormal condition with reduced operational burden, thus achieving efficient diagnosis.

Although, in the above-described exemplary embodiments, each component is achieved by circuits, an embodiment may be achieved, for example, by software executed by a central processing unit (CPU) of a computer. It goes without saying that a storage medium storing the software also constitutes the present embodiment.

Figure 13:
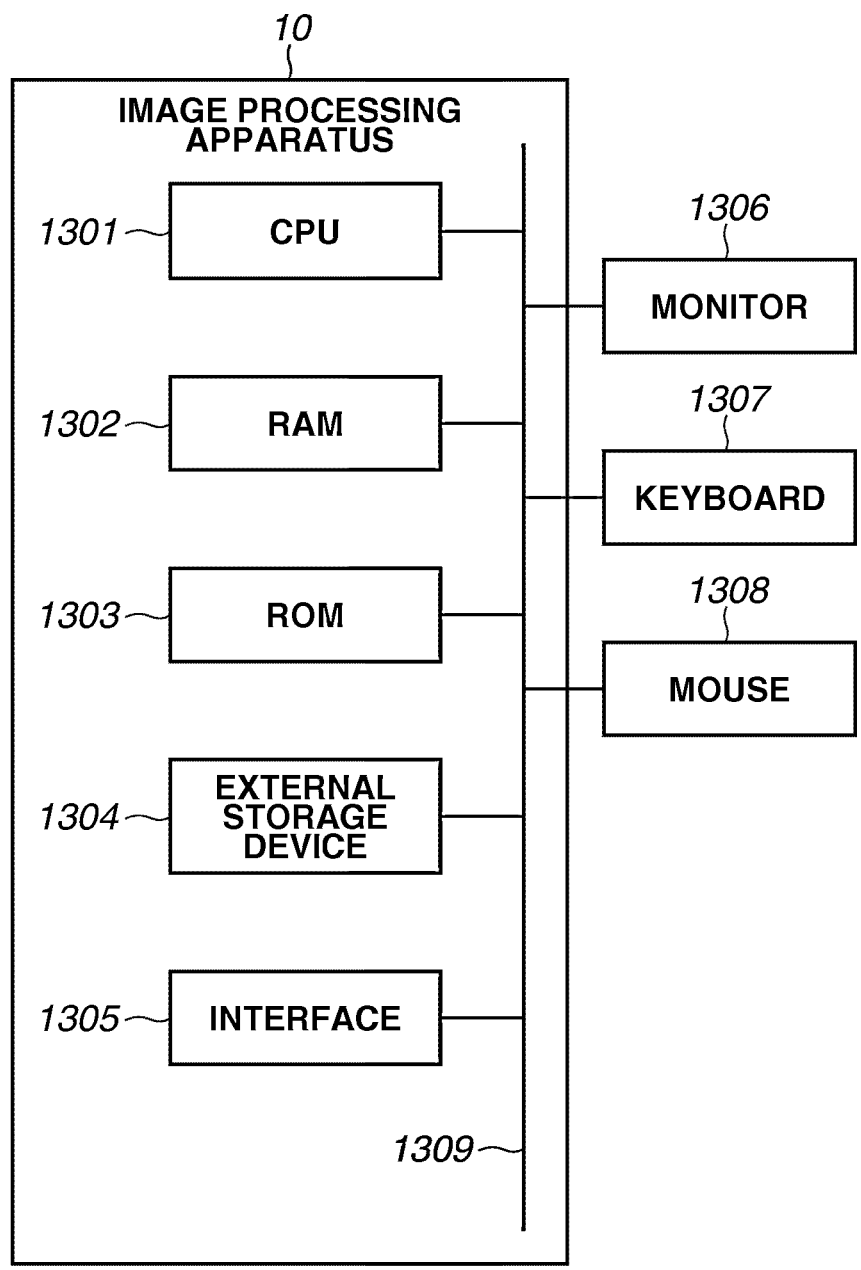
FIG. 13 is a block diagram illustrating a hardware configuration for achieving the image processing apparatus through the collaboration of software and hardware according to the exemplary embodiment.

A hardware configuration for achieving the above-described image processing apparatus 10 through the collaboration of software and hardware will be described below with reference to FIG. 13. Referring to FIG. 13, the image processing apparatus 10 includes a CPU 1301, a memory (random access memory (RAM)) 1302, a control memory (read-only memory (ROM)) 1303, and an external storage 1304 which are all connected via a bus 1309. The image processing apparatus 10 further includes a monitor 1305, a keyboard 1306, a mouse 1307, and an interface 1308 connected thereto.

Figure 9:
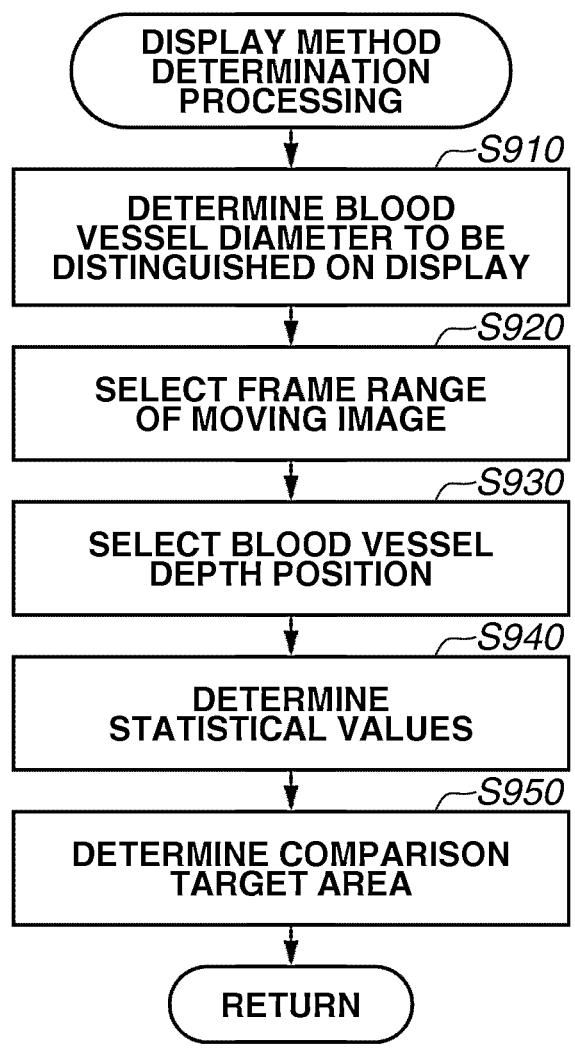
FIG. 9 is a flowchart illustrating detailed processing performed in step S540 in FIG. 5 according to the exemplary embodiment.

To achieve image processing functions according to the above-described exemplary embodiments, control programs for executing the processing illustrated in the flowcharts in FIGS. 5, 8, and 9, and data pieces to be used during execution of the control programs are stored in the external storage 1304.

The control programs and data pieces are suitably stored in the RAM 1302 via the bus 1309 under control of the CPU 1301, and executed by the CPU 1301 to function as each unit (describes below).

For example, the monitor 1305, the keyboard 1306, and the mouse 1307 function as the operation unit 150. The monitor 1305 functions as the display unit 190, and the interface 1308 functions as the SLO image acquisition unit 100 and the volume image acquisition unit 110. The CPU 1301 functions as the structure identification unit 130, the measurement data acquisition unit 140, the determination unit 160, the display control unit 170, and the instruction acquisition unit 180.

Although the above-described image processing apparatus 10 is achieved through the collaboration of a computer including a CPU and software, each function block of the image processing apparatus 10 may be implemented as a circuit. A group of circuits is not limited to a function block, and a part of functions may be implemented as a circuit.

Further, the image processing apparatus 10 may be an image processing system including a plurality of apparatuses.

Aspects of the present embodiment can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

Since the image processing apparatus 10 according to an exemplary embodiment can display the blood flow state by depth, a user can distinctively grasp the blood flow state at respective depth positions. Accordingly, the user can find a depth position at which an abnormal condition occurs in a blood vessel.

Further, since the image processing apparatus 10 according to another exemplary embodiment can display the blood flow state by blood vessel diameter, a user can determine whether an abnormal condition occurs in a thick blood vessel (having a large diameter) affecting a wide retinal area or in a thin blood vessel (having a small diameter) affecting a local retinal area.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-040274 filed Feb. 25, 2011, which is hereby incorporated by reference herein in its entirety.

What is claimed is:

1. An image processing apparatus comprising:
   an identification unit configured to identify a retinal blood vessel based on a first retinal image;
   a measurement unit configured to measure blood flow information for the blood vessel based on the first retinal image; and
   a blood vessel depth position determination unit configured to determine a depth position of the blood vessel based on a second retinal image; and
   a display control unit configured to display the measured blood flow information by at least one selected from the depth position of the identified blood vessel, a size of the identified blood vessel, and a combination of both.

2. The image processing apparatus according to claim 1, wherein the measurement unit measures a blood flow velocity of the blood vessel, and
   wherein the display control unit displays the measured blood flow velocity by the identified depth position of the blood vessel.

3. The image processing apparatus according to claim 1, wherein the identification unit identifies a size of the retinal blood vessel,
   wherein the measurement unit measures a blood flow rate of the blood vessel based on the blood flow velocity measured from the first retinal image and the identified depth position of the blood vessel, and
   wherein the display control unit displays the measured blood flow rate by the identified depth position of the blood vessel.

4. The image processing apparatus according to claim 1, wherein the identification unit identifies a size of the retinal blood vessel based on the first retinal image,
   wherein the measurement unit measures a blood flow velocity of the blood vessel, and
   wherein the display control unit displays the measured blood flow velocity by the identified size of the blood vessel.

5. The image processing apparatus according to claim 1, wherein the identification unit identifies a size of the retinal blood vessel,
   wherein the measurement unit measures a blood flow rate of the blood vessel based on the blood flow velocity measured from the first retinal image and the identified size of the blood vessel, and
   wherein the display control unit displays the measured blood flow rate by the identified size of the blood vessel diameter.

6. The image processing apparatus according to claim 1, wherein the first retinal image is a scanning laser ophthalmoscope (SLO) image captured by an SLO imaging unit, and
   wherein the display control unit divides the SLO image into a plurality of division areas and displays a blood flow velocity for each division area.

7. The image processing apparatus according to claim 1, wherein the measurement unit measures a blood flow velocity based on a plurality of retinal images which are repetitively captured over a fixed time period.

8. The image processing apparatus according to claim 7, wherein the measurement unit measures the blood flow velocity after excluding images having an image quality less than a predetermined threshold value from the plurality of retinal images.

9. The image processing apparatus according to claim 1, wherein the first retinal image is an SLO image captured by an SLO imaging unit, and
   wherein the display control unit divides the SLO image into a plurality of division areas and displays a blood flow rate for each division area.

10. The image processing apparatus according to claim 1, wherein the first retinal image is an SLO image captured by an SLO imaging unit which includes an aberration measurement unit and an adaptive optical system.

11. The image processing apparatus according to claim 1, wherein the identification unit identifies capillaries in the vicinity of a macular portion or an optic disc.

12. An image processing system comprising:
    an image processing apparatus according to claim 1; and
    a display unit configured to display information in accordance with control by the display control unit.

13. An image processing apparatus according to claim 1, wherein the second retinal image is a tomographic (OCT) image captured by an optical coherence tomographic imaging unit.

14. An image processing apparatus according to claim 1, comprising a structure identification unit configured to detect ocular layer boundaries in the second retinal image, and
    wherein the blood vessel depth position determination unit determines a depth position of the blood vessel in relation to the detected ocular layer boundaries in the second retinal image.

15. An image processing apparatus according to claim 1, wherein the blood vessel depth position determination unit determines whether the depth position of the blood vessel corresponds to a surface capillary area or a deep capillary area in the second retinal image.

* * * * *